(12) United States Patent
Shen et al.

(10) Patent No.: US 7,498,593 B2
(45) Date of Patent: Mar. 3, 2009

(54) TERAHERTZ RADIATION SOURCES AND METHODS

(75) Inventors: Yao-chun Shen, Cambridge (GB); Edmund H. Linfield, Cambridge (GB); Alexander G. Davies, Leeds (GB)

(73) Assignee: Cambridge University Technical Services Limited, Cambridge (GB)

( * ) Notice: Subject to any disclaimer, the term of this patent is extended or adjusted under 35 U.S.C. 154(b) by 214 days.

(21) Appl. No.: 10/550,620

(22) PCT Filed: Mar. 24, 2004

(86) PCT No.: PCT/GB2004/001261

§ 371 (c)(1),
(2), (4) Date: May 25, 2006

(87) PCT Pub. No.: WO2004/086560

PCT Pub. Date: Oct. 7, 2004

(65) Prior Publication Data

US 2007/0034813 A1    Feb. 15, 2007

(30) Foreign Application Priority Data

Mar. 27, 2003  (GB)  .................. 0307096.8

(51) Int. Cl.
*A61N 5/06* (2006.01)
*G01J 3/10* (2006.01)
*H05G 2/00* (2006.01)

(52) U.S. Cl. ................ 250/504 R; 250/330; 250/338.1; 250/338.4; 250/358.1; 250/341.1; 250/341.8; 250/503.1; 250/492.24; 250/493.1; 250/494.4; 250/494.22; 257/E33.04; 372/5

(58) Field of Classification Search ............. 250/504 R, 250/330, 338.1, 338.4, 358.1, 341.1, 341.8, 250/503.1, 492.24, 493.1, 494.4, 494.22; 257/E33.04; 372/5
See application file for complete search history.

(56) References Cited

U.S. PATENT DOCUMENTS

| 4,972,069 A | 11/1990 | Grischkowsky |
| 5,894,125 A * | 4/1999 | Brener et al. ............... 250/330 |
| 2001/0038074 A1 | 11/2001 | Zhang et al. |

FOREIGN PATENT DOCUMENTS

| EP | 0 828 143 A2 | 3/1998 |
| WO | WO 01/38929 A1 | 5/2001 |

OTHER PUBLICATIONS

Nuss et al., "Terahertz Time-Domain Spectroscopy", Millimeter and Submimillimeter Wave Spectroscopy of Solids, ed. G.Gruner, Berlin Springer, pp. 7-50, (1998).

(Continued)

*Primary Examiner*—David A. Vanore
*Assistant Examiner*—Meenakshi S Sahu
(74) *Attorney, Agent, or Firm*—Dickstein Shapiro LLP

(57) ABSTRACT

The invention relates to improved terahertz radiation sources and associated methods. A terahertz radiation source is described, comprising: an emitter (202) comprising a semiconductor material (12); a pair of electrodes (204a,b) adjacent a face of said semiconductor, said pair of electrodes defining a gap between said electrodes; a pulsed light source input for illuminating said semiconductor to excite photocarriers in said semiconductor to generate terahertz radiation; and a radiation collector (212) to collect said terahertz radiation; and wherein said radiation collector is disposed on the same side of said semiconductor as said electrodes. A related method of providing terahertz radiation is also described.

23 Claims, 10 Drawing Sheets

OTHER PUBLICATIONS

Beard et al., "Terahertz Spectroscopy", *J. Phys. Chem. B.*, vol. 106, pp. 7146-7159, (2002).

Zhang, "Terahertz wave Imaging: Horizons And Hurdles", *Phys. Med. Biol.*, vol. 47, pp. 3667-3677, (2002).

Zhang et al., "Optoelectronic Measurement Of Semiconductor Surfaces And Interfaces With Femtosecond Optics", *J. Appl. Phys.*, vol. 71, No. 1, pp. 326-338, (1992).

Dekorsy et al., "THz Electromagnetic Emission By Coherent Infrared-Active Phonons", *Phys. Rev. B*, vol. 53, No. 7, pp. 4005-4014, (1996).

Kono, et al., "Temperature Dependence Of Terahertz Radiation for n-type InSb and n-type InAs Surfaces", *Appl. Phys. B.*, vol. 71, pp. 901-904, (2000).

Davies et al., "The Development Of Terahertz Sources And Their Applications", *Phys. Med. Biol.*, vol. 47, pp. 3679-3680, (2002).

Ma et al., "Determination of Ratios Between Nonlinear-Optical Coefficients By Using Subpicosecond Optical Retification", *J. Opt. Soc. Am. B*, vol. 10, No. 7, pp. 1175-1179, (1993).

Saeta et al., "Short Terahertz Pulses From Semiconductor Surfaces: The Importance Of Bulk Difference-Frequency Mixing", *Appl. Phys. Lett.*, vol. 63, No. 25, pp. 3483-3484, (1993).

Joffre et al., "Femtosecond Diffracting Fourier-Transform Infrared Interferometer", *Optics Letters*, vol. 21, No. 13, pp. 964-966, (1996).

Wu et al., "Free-Space Electro-Optics Sampling Of Mid-Infrared Pulses", *Appl. Phys. Lett.*, vol. 71, No. 10, pp. 1285-1286, (1997).

Darrow et al., "Saturation Properties of Large-Aperture Photoconducting Antennas", *IEEE Jour. Quantum Elec.*, vol. 28, No. 6, pp. 1607-1616, (1992).

Leitenstorfer, et al., "Detectors and Sources For Ultrabroadband Electro-Optic Sampling: Experiment And Theory", *Appl. Phys. Lett.*, vol. 74, No. 11, pp. 1516-1518, (1999).

Auston et al., "Picosecond Photoconducting Hertzian Dipoles", *Appl. Phys. Lett.*, vol. 45, No. 3, (1984).

Grischkowsky, "Optoelectronic Characterization of Transmission Lines and Waveguides by Terahertz Time-Domain Spectroscpy", *IEEE J. Sel. Topics Quantum Electron.*, vol. 6, No. 6, pp. 1122-1135, (2000).

Holzman et al., "Recombination-Independent Photogeneration Of Ultrashort Electrical Pulses", *App. Phys. Lett.*, vol. 76, No. 2, pp. 134-136, (2000).

Holzman et al., "Ultrafast Photoconductive Self-Switching of Subpicosecond Electrical Pulses", *IEEE J. Quantum Electron.*, vol. 36, No. 2, pp. 130-136, (2000).

Krokel et al., "Subpicosecond Electrical Pulse Generation Using Photoconductive Switches With Long Carrier Lifetimes", *Appl. Phys. Lett.*, vol. 54, No. 11, pp. 1046-1047, (1989).

Lieitenstorfer et al., "Femtosecond High-Field Transport in Compound Semiconductors", *Physical Review B*, vol. 61, No. 24, pp. 16642-16648, (2001).

Huber et al., "Generation and Field-Resolved Detection Of Femtosecond Electromagnetic Pulses Tunable Up To 41 THz", *App. Phys. Lett.*, vol. 76, No. 22, pp. 3191-3193, (2000).

* cited by examiner

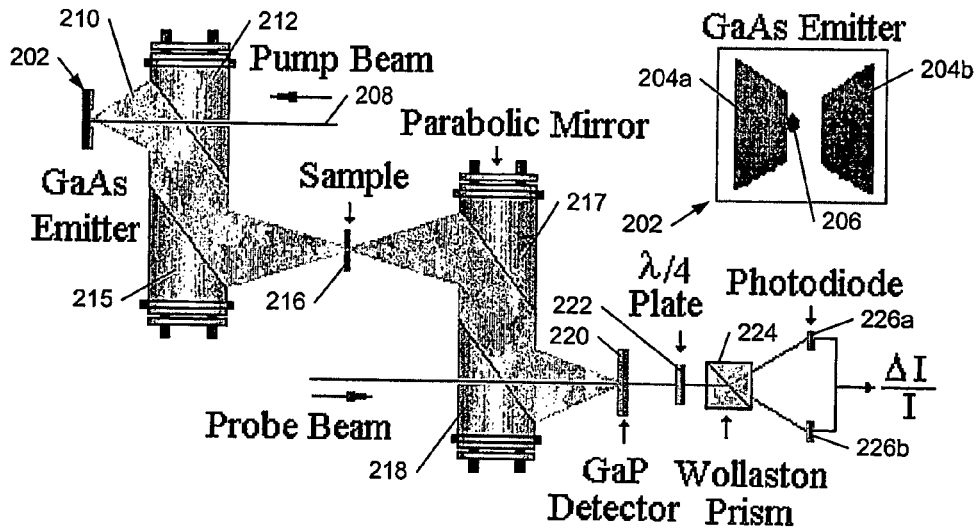
Figure 2b
Figure 2a
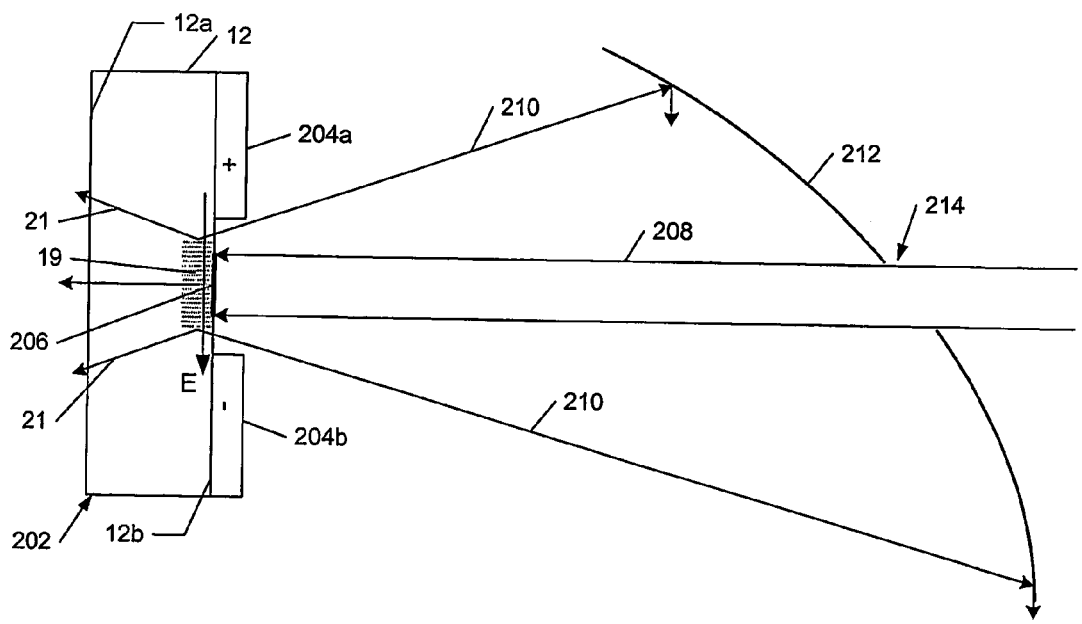
Figure 2c

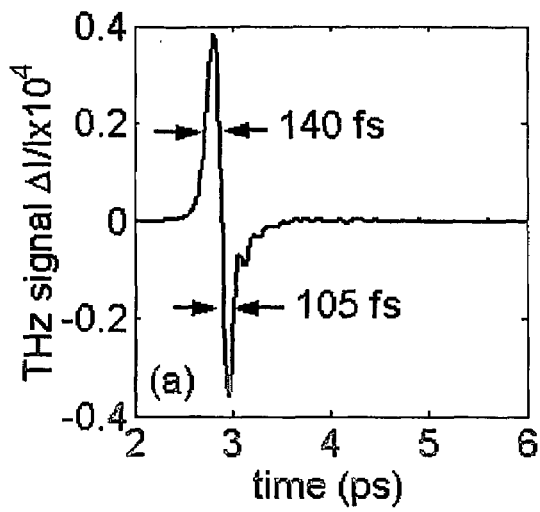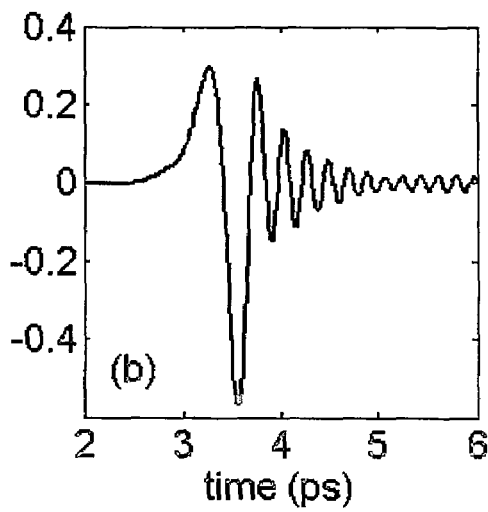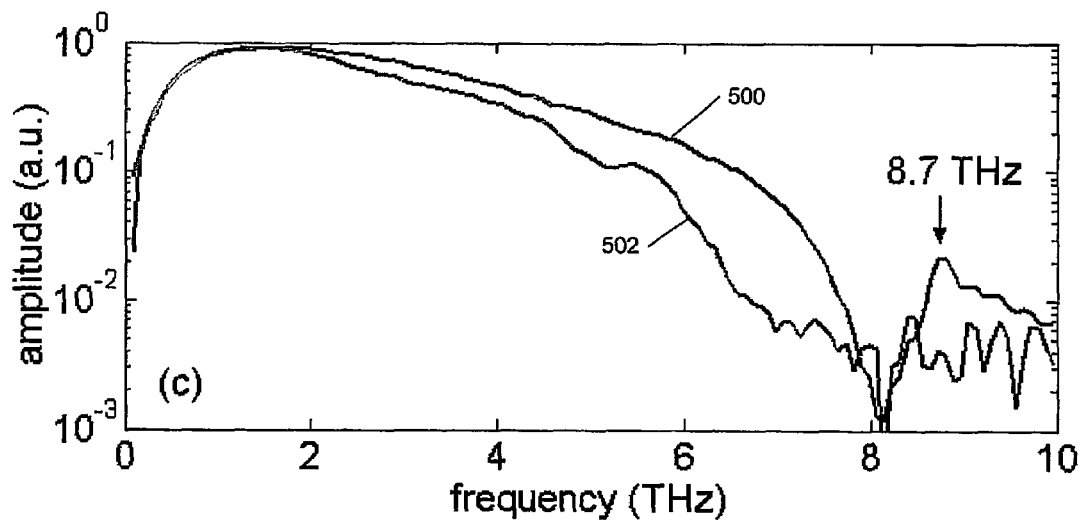
Figure 5c

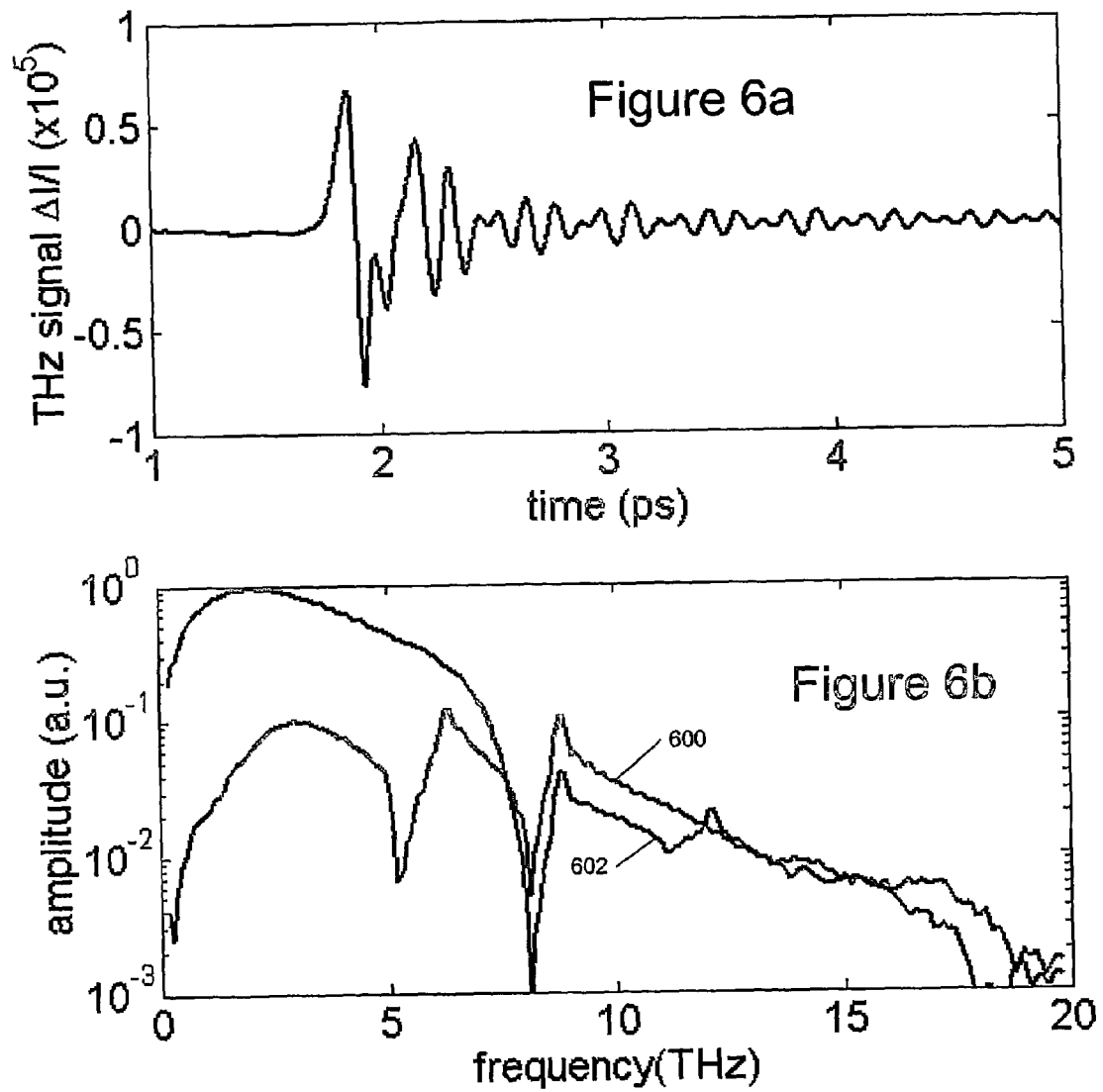

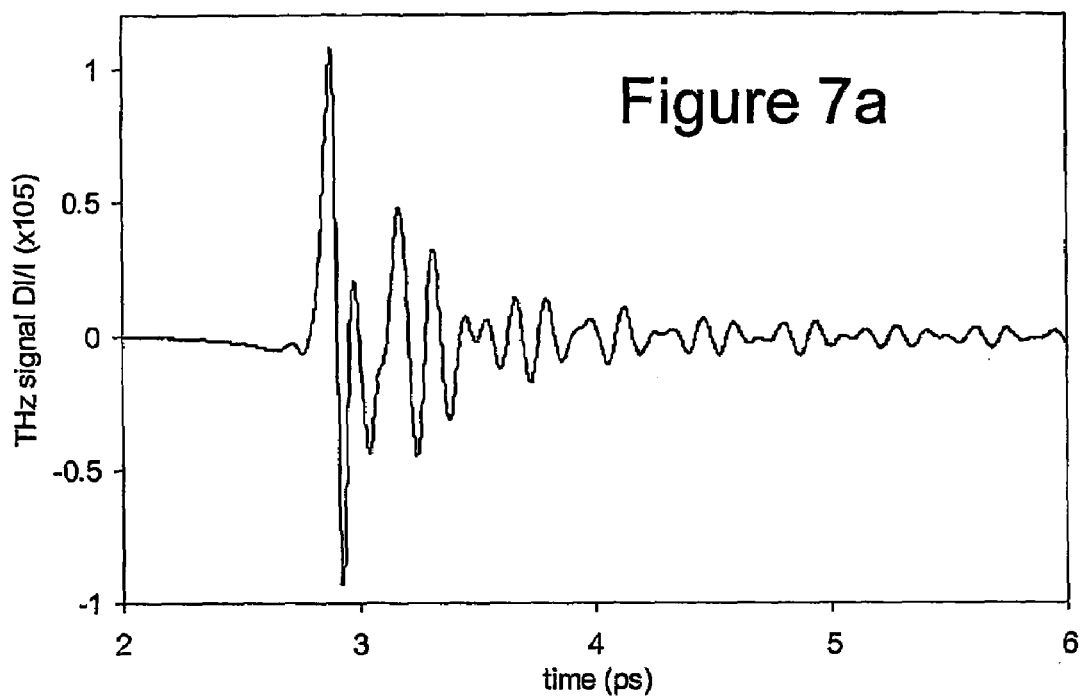
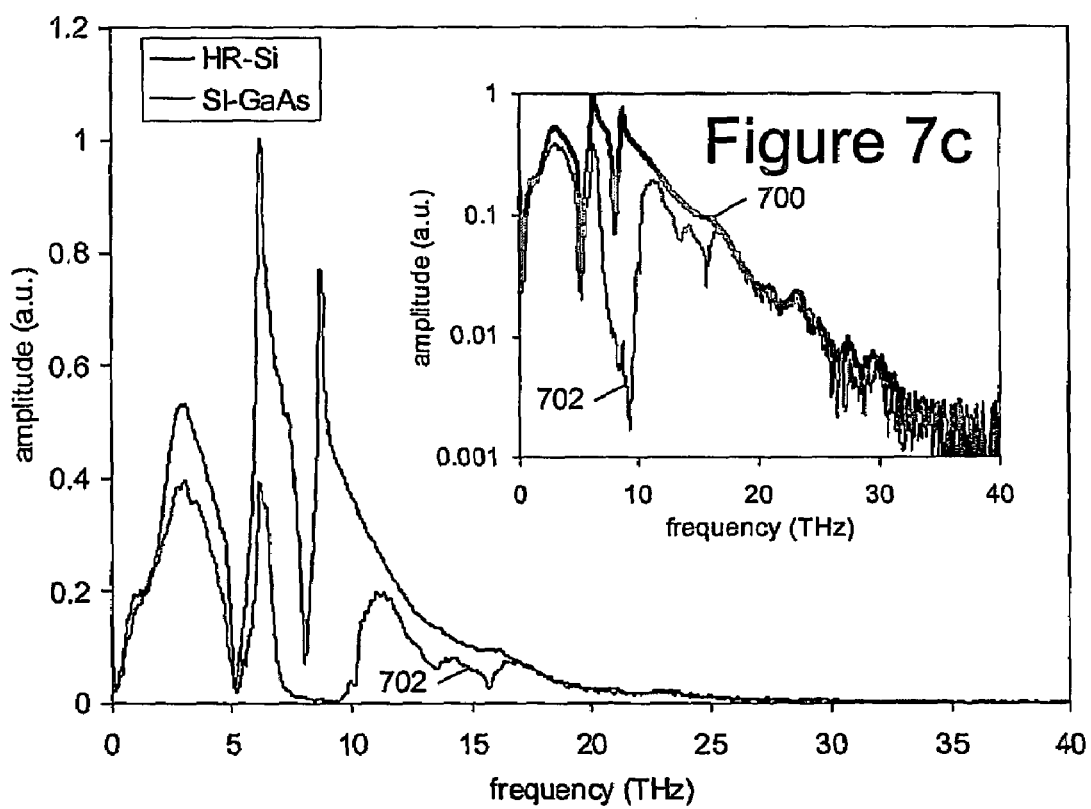
Figure 7b

TERAHERTZ RADIATION SOURCES AND METHODS

This invention relates to improved terahertz radiation sources and associated methods.

The terahertz (THz) region of the electromagnetic spectrum spans the frequency range between the mid-infrared and the millimeter/microwave portion of the spectrum. In this specification, terahertz radiation is considered to be that lying within a frequency range of from 0.1 THz to 100 THz.

There are many potential applications for terahertz radiation, including time-domain spectroscopy and imaging (see, for example, M. C. Nuss and J. Orenstein, in Millimeter and Submillimeter Wave Spectroscopy of Solids, ed G Grüner, (Berlin, Springer, 1998) and reference therein, M. C. Beard, G. M. Turner, and C. A. Schmuttenmaer, J. Phys. Chem. B 106, 7146(2002), X.-C. Zhang, Phys. Med. Biol. 47, 3667 (2002)). However, it is difficult to generate radiation in the terahertz region of the spectrum, particularly in the higher frequency portions of the terahertz range.

Some known techniques for the generation of terahertz radiation include surface field generation, with or without an applied magnetic field (see, for example X.-C. Zhang and D. H. Auston, J. Appl. Phys. 71, 326 (1992), T. Dekorsy, H. Auer, H. J. Bakker, H. G. Roskos, and H. Kurz, Phys. Rev. B 53, 4005(1996), S. Kono, P. Gu, M. Tani, and K. Sakai, Appl. Phys. B 71, 901 (2000), A. G. Davies, E. H. Linfield and M. B. Johnston, Phys. Med. Biol. 47, 3679 (2002) and electro-optic based techniques, such as optical rectification or difference frequency mixing (see, for example X. F. Ma and X.-C. Zhang, J. Opt. Soc. Am. B 10, 1175 (1993) and P. N. Seeta, B. I. Greene, and S. L. Chuang, Appl. Phys. Lett. 63, 3482 (1993); M. Joffre, A. Bonvalet, A. Migus, and J.-L Martin, Opt. Lett. 21, 964 (1996); Q. Wu and X.-C. Zhang, Appl. Phys. Lett. 71, (1997); US 2001/0038074; U.S. Pat. No. 4,972,069).

Non-linear optical techniques for the generation of terahertz radiation have been the subject of some interest because they appear to have potential for the generation of terahertz power at relatively high frequencies, possibly up to 37 THz. However, these devices are only able to produce very small amounts of energy at low repetition rates, for example of the order of 1 KHz using a mechanical chopper. Similarly frequency components as high as 60 THz have been generated from GaAs p-i-n diodes ((A. Leitenstorfer, S. Hunsche, J. Shah, M. C. Nuss, and W. H. Knox, Phys. Rev. Lett. 82, 5140 (1999); Phys. Rev. B. 61, 16642, 2000) but these are complex and difficult to fabricate, and again have a very low power output. By contrast, photoconductive emitters are more efficient, potentially by orders of magnitude, and can be configured to operate at a much higher repetition rate, which is important for applications such as spectroscopic or imaging applications, since the data collection time can be reduced. However, a disadvantage of these photoconductive terahertz emitters is their relatively low upper frequency limit, which is generally around 5 THz.

Some examples of photoconductive terahertz emitters are described in D. H. Auston, K. P. Cheung, and P. R. Smith, Appl. Phys. Lett. 45, 284 (1984) and D. R. Grischkowsky, IEEE J. Sel. Topics Quantum Electron. 6, 1122 (2000); J. F. Holzman, F. E. Vermeulen, and A. Y. Elezzabi, Appl. Phys. Lett. 76, 134 (2000); IEEE J. Quantum Electron. 36, 130 (2000); D. Krokel, D. Grischkowsky, and M. B. Ketchen, Appl. Phys. Lett. 54, 1046 (1989).

Broadly speaking, the best photoconductive emitter presently known is that devised by Bell Labs, as described for example in EP-A-0 828 143 (Lucent Technologies Inc). Since its invention, therefore, skilled workers in the field have adopted the configuration of this device (see, for example, WO 01/38929). FIG. 1a shows the main features of such a device.

The device 10 of FIG. 1a comprises a semiconductor 12, optionally mounted on a substrate, bearing a pair of electrodes 14a, b. Pulsed laser illumination 16 impinges on a gap 18 between the electrodes, causing the generation of terahertz radiation as described in more detail below. This radiation propagates through the semiconductor material 12 and is collected and collimated by a silicon lens 20 to provide a collimated terahertz radiation output beam 22. The semiconductor 12 has a front surface 12a, through which the terahertz radiation is emitted and a rear surface 12b, upon which the pulsed laser impinges. The silicon lens 20 is mounted adjacent front surface 12a for practical convenience (since it would interfere with the laser beam if mounted on the other side of the semiconductor) and also to assist coupling of the terahertz radiation from the semiconductor into the silicon lens, and in particular to reduce reflections at the substrate/lens interface.

FIG. 1b shows more details of the device of FIG. 1a, and illustrates operation of the device. A voltage is applied across electrodes 14a, b, setting up an electric field E across the semiconductor 12 as shown. The pulsed laser 16 is focussed to a spot 17 on the surface of the semiconductor, resulting in the generation of photocarriers in region 19 adjacent surface 12b of the semiconductor, the terahertz radiation 21 then propagating towards face 12a for collection by the lens (not shown in FIG. 1b). Optionally, the semiconductor 12 may be mounted on a substrate located between face 12a and the lens (not shown in FIG. 1b).

The frequency of the terahertz radiation emitted is dependent upon the pulse width (or at least the edge rise-time) of laser beam 16, and a laser which is able to provide a sub-picosecond pulse width is therefore preferably used, to provide radiation frequencies greater than 1 THz. The laser wavelength is selected to be suitable for optically exciting carriers in the semiconductor material 12 and may comprise, for example, a Ti:Sapphire laser or an Erbium-doped fibre laser. The semiconductor material may comprise, for example, Gallium Arsenide or a variant thereof, such as LT-GaAs (low temperature-grown Gallium Arsenide) or SI-GaAs (semi-insulating GaAs), or radiation-damaged silicon-on-sapphire (RD-SOS), or Indium Gallium Arsenide or InGaAs/InAlAs quantum wells (see EP'143 above and the references therein). Details of electrode materials and dimensions are given later; further examples of electrodes are described in EP'143 mentioned above, hereby incorporated by reference in its entirety.

In operation, laser pulse 16 generates electron-hole pairs and these photo-excited carriers are accelerated by the biasing electric field E. Thus the current through the device rises very rapidly after an optical pulse and then decays with a time constant determined by the carrier lifetime of the semiconductor. The physical separation of the holes and electrons forms a macroscopic space-charge field having a direction opposite to the biasing field, and thus screens the externally applied biasing field. From Maxwell's equations the fast temporal change of the electric field produces a displacement current pulse, thus generating pulsed electromagnetic radiation in the terahertz region of the spectrum. Theoretical simulations suggest that a sub-100 femtosecond (fs) electrical pulse is obtainable but in practice 350 fs terahertz radiation pulses are among the shortest obtained with Gallium Arsenide emitters.

There therefore exists a need for improved terahertz radiation sources and methods. The inventor has recognised that there are advantages in (broadly speaking) inverting the conventional photoconductive terahertz emitter structure which has been used heretofore.

Thus in a first aspect the invention provides a terahertz radiation source comprising: an emitter comprising a semiconductor material having two sides; a pair of electrodes on one side of said semiconductor; a pulsed light source input for illuminating said semiconductor to excite photo-carriers in said semiconductor to generate terahertz radiation; and a radiation collector to collect said terahertz radiation; and wherein said radiation collector is disposed on the same side of said semiconductor as said electrodes.

In a related aspect the invention also provides a terahertz radiation source comprising: a semiconductor having opposed first and second faces; a pair of electrodes adjacent one of said faces of said semiconductor; a pulsed light source input for illuminating said semiconductor to excite photo-carriers in said semiconductor to generate terahertz radiation; and a radiation collector to collect said terahertz radiation; and wherein said radiation collector is configured to collect said terahertz radiation from said one of said faces of said semiconductor without said collected radiation having passed through the other of said faces.

Roughly speaking, instead of collecting terahertz radiation emitted in a forwards direction, a backwards collection scheme is employed. Thus in embodiments terahertz radiation emitted from the surface of the emitter bearing the electrodes is collected, thus reducing the effects of dispersion and absorption in the semiconductor material. As will be described later in embodiments this facilitates the production of terahertz radiation with components at significantly higher frequencies than previously available from photoconductive-type emitters.

The emitter preferably comprises a III-V semiconductor slab or wafer, optionally supported on a substrate. Preferably the emitter is relatively thin to facilitate cooling from the non-electrode bearing surface, although it will be recognised that since terahertz radiation in a 'backwards' direction is being collected the precise thickness or configuration of the semiconductor and/or substrate is not important. The electrodes may be formed on the surface of the semiconductor or may be buried within the surface by means of conventional fabrication techniques well known in the art.

The pulsed light source preferably comprises a pulsed laser with at least a fast rising edge, preferably less than 1 picosecond, more preferably less than 0.1 picosecond. The laser is preferably configured to illuminate the gap between the electrodes (although transparent or very thin electrodes could be employed), and preferably the laser light is focussed to a spot located asymmetrically within the gap between the electrodes.

The radiation collector may comprise a lens such as a silicon lens, or a mirror such as a parabolic mirror. Since metal reflects terahertz radiation a metal mirror may be employed. In some embodiments the radiation collector, for example the mirror, is provided with an aperture for illuminating the semiconductor using the laser beam. In other embodiments a small diagonal mirror may be provided between the semiconductor and the radiation collector, for directing light from a laser onto the semiconductor. In still other embodiments oblique laser illumination may be employed.

In embodiments, since terahertz radiation is collected in a 'backwards' direction, the 'front' face of the emitter may be provided with a cooling device. This may comprise a passive cooling device such as a heat sink or heat pipe, or an active device such as a device employing circulated coolant or a Peltier effect device.

Thus in a further aspect the invention provides a terahertz emitter comprising a semiconductor having first and second electrodes adjacent a first face of said semiconductor for applying an electric field to the semiconductor, said first and second electrodes defining a gap there between; and a heat transfer device mounted adjacent a second face of said semiconductor substantially opposite said first face; and wherein at least a portion of said heat transfer device is disposed substantially opposite said gap.

The invention further provides a source of terahertz radiation comprising a housing, said housing holding a semiconductor, said semiconductor bearing a pair of electrodes adjacent one surface of said semiconductor; means for directing a pulsed laser onto said semiconductor to generate terahertz radiation; and means for providing said terahertz radiation from said source; and characterised in that said providing means is disposed to face said electrode-bearing semiconductor surface.

In embodiments the terahertz radiation may be provided by means of an aperture in the housing and, optionally, the same aperture may be used for illuminating the semiconductor. Additionally or alternatively some other means for directing a pulsed laser beam onto the semiconductor may be employed, such as a fibre optic.

In a related aspect the invention also provides a method of providing terahertz radiation from a photoconductive terahertz radiation source, the source comprising a semiconductor with electrodes adjacent an excitation surface of the said semiconductor, the method comprising applying an electric field to said electrodes directing a pulsed laser beam towards said excitation surface; and using terahertz radiation emitted out of said excitation surface for providing said terahertz radiation.

The invention further provides a method of providing terahertz radiation from a photoconductive terahertz radiation source, the source comprising a semiconductor with electrodes adjacent a surface of the said semiconductor, the method comprising applying an electric field to said electrodes; and directing a pulsed laser beam towards said semiconductor surface, wherein a normal to said semiconductor surface with a component in a direction of propagation of said laser beam defines a forward direction; and wherein the method further comprises collecting said terahertz radiation in a reverse direction, substantially opposite to said forwards direction.

The terahertz radiation preferably comprises radiation occupying a portion of a frequency range of from 0.1 THz to 100 THz, and more particularly within a portion of a frequency range of from 0.1 THz to 30 THz. Generally the optical excitation will result in terahertz radiation across a band of frequencies, as illustrated later, to some extent the band being variable dependent upon the pulse width of the laser light source. The skilled person will further recognise that in this document 'light' is not restricted to visible light but includes infrared and ultraviolet light up to x-rays (atto-second pulses have recently been realised in the x-ray range), and 'illumination' is to be construed accordingly.

The skilled person will recognise that features from some of the above-described aspects of the invention and embodiments may be combined with other aspects of the invention.

The above and other aspects of the invention will now be further described, by way of example only, with reference to the accompanying figures in which;

FIGS. 1a and 1b show, respectively, a known photoconductive terahertz radiation source, and details of the operation of the source of FIG. 1a;

FIGS. 2a to 2g show, respectively, a terahertz radiation source and detection system in accordance with a first embodiment of the present invention, an electrode configuration for the apparatus of FIG. 2a, a schematic diagram showing details of the terahertz source of FIG. 2a, a terahertz radiation source according to a second embodiment of the invention, a terahertz radiation source according to a third embodiment of the invention, a terahertz radiation source according to a fourth embodiment of the invention, and a terahertz radiation source according to a fifth embodiment of the invention;

FIG. 5a to 5c show a time-domain terahertz radiation signal for radiation emitted in a backwards direction, a time-domain terahertz radiation signal for radiation emitted in a forwards direction, and frequency spectra for the radiation signals of FIGS. 5a and 5c;

FIGS. 6a and 6b show a second time-domain terahertz radiation signal, and corresponding frequency spectra;

FIGS. 7a to 7c show a time-domain terahertz radiation signal, and corresponding frequency spectra on linear and on logarithmic scales respectively.

Figure 1A:
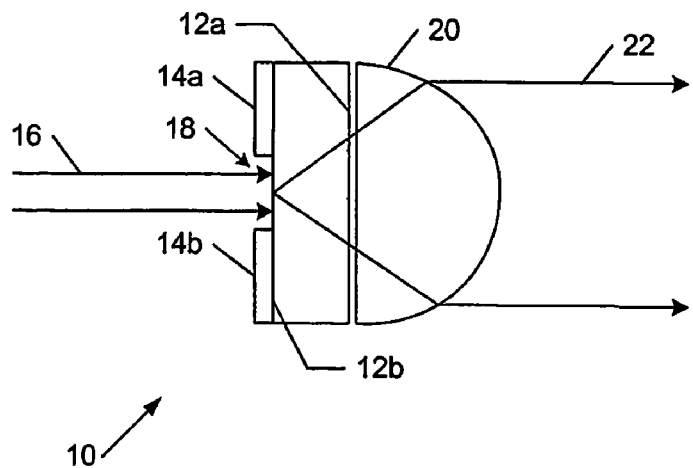

Referring first to FIG. 2a this shows a schematic diagram of an experimental arrangement 200 for the generation and detection of terahertz radiation. FIG. 2b (inset) shows a schematic diagram of an example electrode geometry for the arrangement of FIG. 2a.

Referring to FIGS. 2a and 2b, a photoconductive emitter 202 comprises a low-temperature-grown (LT) gallium arsenide (GaAs) substrate, in one constructed embodiment having a thickness of 0.53 mm. In one embodiment the LT-GaAs wafer was grown at the Cavendish Laboratories, University of Cambridge, UK (A2696) and had a carrier life time of 0.4 picoseconds, as estimated from a time-resolved reflectivity measurement. Two NiCr/Au electrodes 204a, b were fabricated on this substrate using vacuum evaporation.

A pump laser beam 208 illuminates the electrode-side of the GaAs emitter 202 and emitted terahertz radiation 210 is collected in the 'backwards' direction using a parabolic mirror 212. In preferred embodiments the parabolic mirror(s) are gold coated mirror(s), in one experimental arrangement approximately 5 cm in diameter. Preferably the terahertz emitting region 19 is located substantially at the focus of parabolic mirror 212 (or of an equivalent lens). Mirror 212 has a small hole 214, for example 1-2 mm in diameter, drilled through it to allow the pump beam 208 to illuminate the emitter 202 (see FIG. 2c). Since the hole 214 can be small the efficiency of the mirror 212 at collecting the terahertz radiation is little affected.

Mirror 212 provides a substantially collimated beam of terahertz radiation to a second parabolic mirror 215, which focuses this radiation onto a sample 216 in the illustrated experimental arrangement. However, the skilled person will appreciate that the collimated beam of terahertz radiation may be used in many ways, including for imaging and spectroscopy.

The radiation which passes through sample 216 is collected by a third parabolic mirror 217 and directed by a fourth parabolic mirror 218 on to a terahertz radiation detector. A variety of suitable detectors is known in the art; for example, EP 0 828 143 A mentioned above describes some examples. In the illustrated arrangement a Gallium Phosphide (GaP) detector 220 is employed, in conjunction with a quarter wave plate 222 and Wollaston prism 224 which provides a differential signal to a pair of a photodiodes 226a, b. These in turn provide a differential output, for example to a lock-in amplifier locked to a driving voltage of the emitter 202.

As can be seen from inspection of FIGS. 2a and 2b, the terahertz radiation is collected 'backwards' as compared with a conventional arrangements. This has a number of advantages, in particular a reduction in dispersion and absorption in the GaAs substrate. There may be a small reduction in power output as compared with a conventional geometry, resulting from the optical coupling/alignment. However, as will be seen from the experimental results described later, this is more than compensated for by an increased power output at higher terahertz frequencies.

The pump laser beam 208 is preferably used for asymmetric excitation of the GaAs emitter, as can be seen from the asymmetric positioning of pump laser beam illumination spot 206 between the electrodes 204a, b of FIG. 2b. Such asymmetric excitation increases the (terahertz) output power, with the indirect effect of increasing the useful bandwidth of the generated terahertz signal, although such asymmetric excitation does not appear to affect the intrinsic bandwidth of the emitter 202.

FIG. 2c shows more details of the terahertz radiation source of FIGS. 2a and 2b, although in this figure and the subsequent figures, for clarity, asymmetric excitation is not shown (although this is preferable).

Figure 1B:
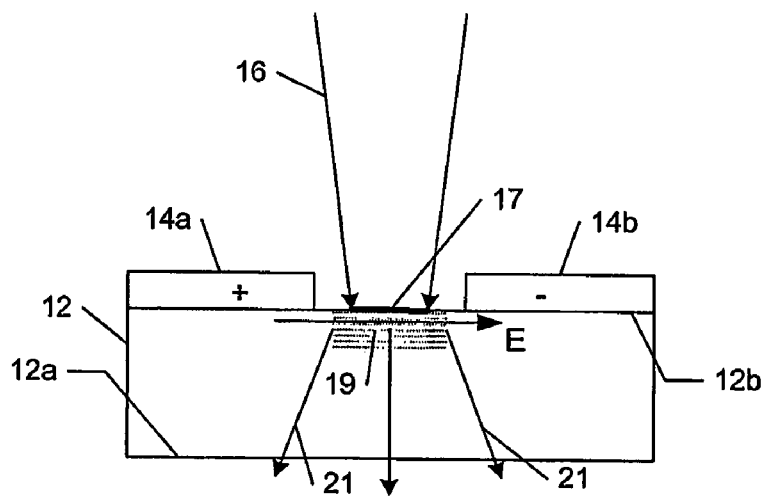

In FIG. 2c like elements to those of FIG. 1b are indicated by like reference numerals, although for clarity the pump laser beam is in this arrangement given the designation 208, the illuminated spot the designation 206, and the electrodes the designations 204a, b. FIG. 2c shows the pump laser beam 208 being provided to the emitter 202 via a hole 214 in the mirror 212.

The substrate semiconductor material is selected in conjunction with the pump laser to have a suitable band gap for photo-excitation of carriers; generally this means that a narrow band gap is preferable. It is further preferable that the semiconductor has a relatively large photocarrier mobility and a relatively high resistivity (that is, preferably, it is undoped). For example, radiation damaged silicon-on-sapphire (RD-SoS) or a III-V semiconductor such as GaAs or GaP may be employed. If a particular terahertz frequency is of interest the semiconductor material may further be selected to aim to avoid phonon absorption at or near this frequency.

The laser wavelength is selected for photo-excitation of carriers, and should preferably provide a few hundred milliwatts of power focused to a spot a few tens of micrometres in diameter. In one experiment a drive voltage of 200 volts peak-to-peak was employed, which gave a current of a few milliamps, thus dissipating a few watts in the emitter. The frequency of the drive is not critical but higher frequencies provide a better signal to noise ratio with a lock-in amplifier since, in effect, more data can be collected in the same time. A frequency of the order of 100 KHz is suitable, although in other arrangements a dc drive may be employed. The electrode gap may be of the order of 0.5 mm, for example in the range 0.1 mm to 1 mm (or smaller); in embodiments electrode gaps of 0.2 mm-0.4 mm have been satisfactorily employed. The substrate thickness is not critical and may be selected for practical convenience; in embodiments a GaAs wafer with a thickness of approximately 0.5 mm was used. To help keep the emitter cool it may be preferable to employ thinner rather thicker substrates.

Figure 2D:
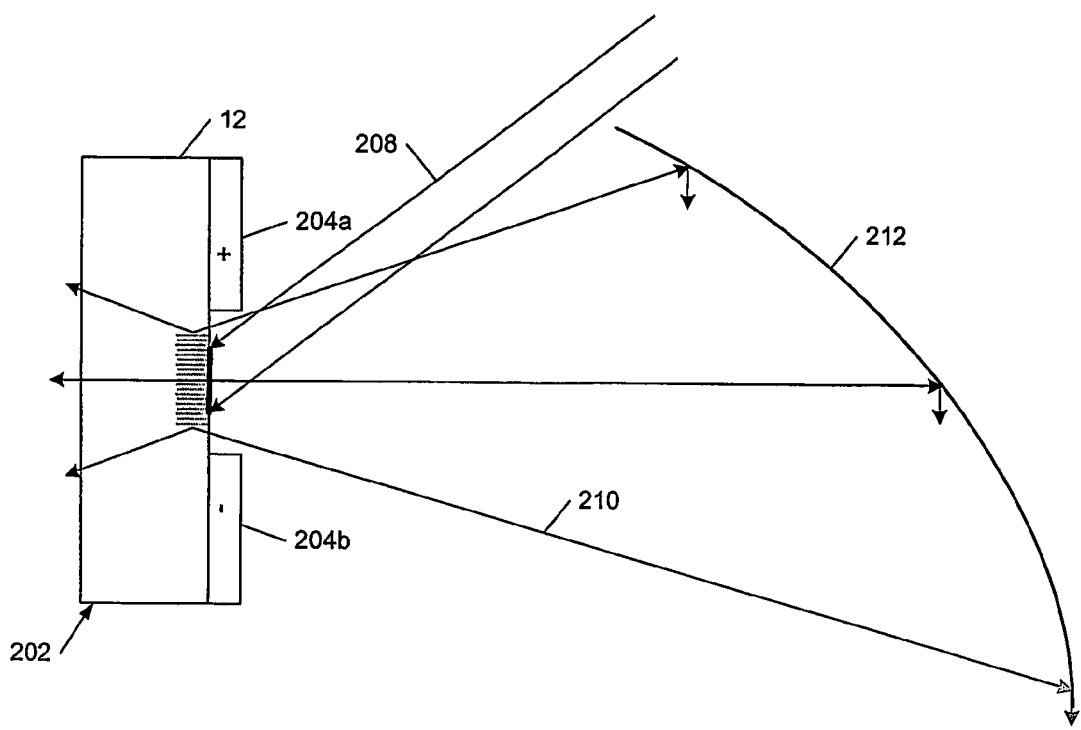
Figure 2E:
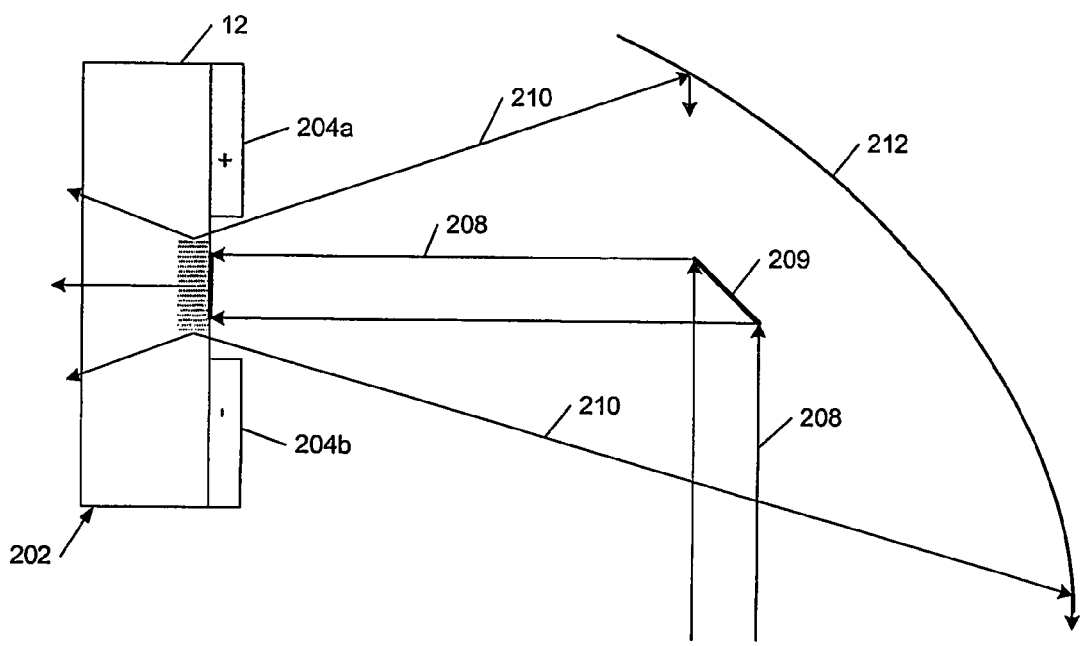

FIG. 2d shows a first alternative embodiment in which the pump laser beam 208 illuminates the emitter 202 from an oblique angle rather than through an aperture in mirror 212. FIG. 2e illustrates a further alternative embodiment in which a small diagonal mirror 209, for example 1-2 mm of metallised foil, is used to direct the pump laser onto the emitter 202. Generally the on-axis pump laser arrangements of FIGS. 2c and 2e are preferable to the off-axis arrangement of FIG. 2d as alignment is more straightforward.

In the embodiments of FIGS. 2d and 2e the paraboloid mirror 212 may be replaced by a lens, for example a fused silica lens below 1 THz or a silicon lens above 1 THz. Some polymers, for example polyethylene or poly-4-methylpentene-1, may also be used as a lens material. Mirrors, however, have some advantages over lens and can provide high reflectivity and achromatic operation over a broad range of terahertz frequencies, and in particular at higher terahertz frequencies.

Figure 2F:
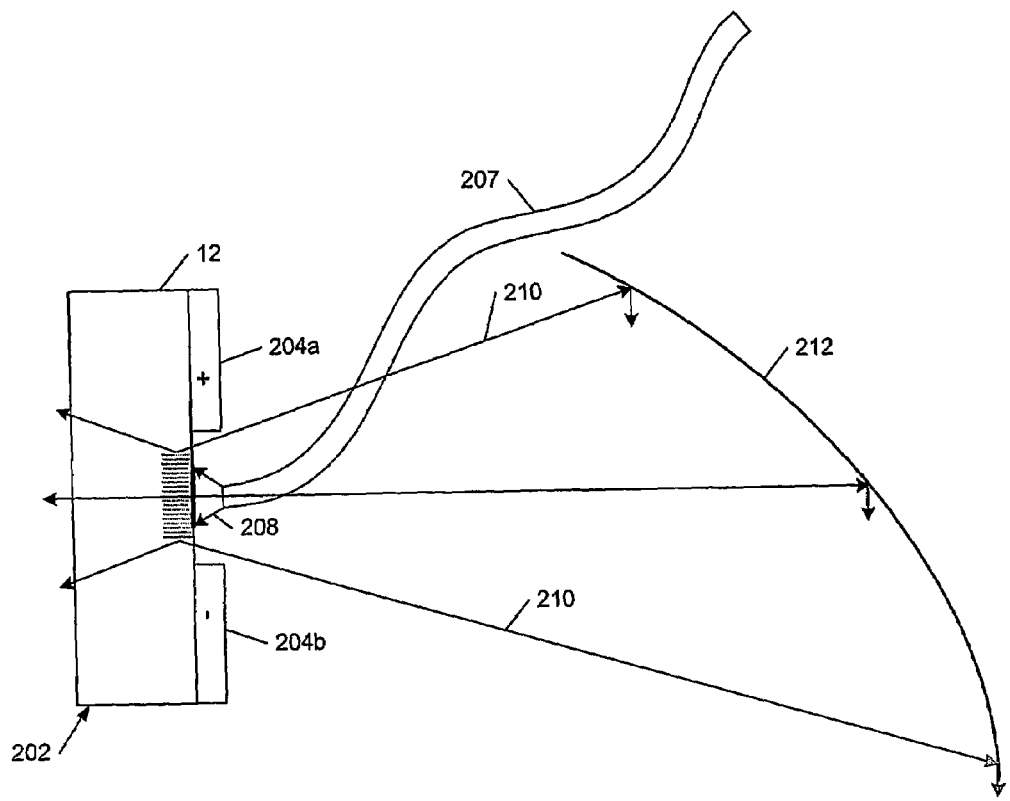

FIG. 2f illustrates a further alternative embodiment, again lacking a hole in mirror 212, in which a fibre optic 207 is used to deliver the pump laser to the semiconductor 12.

Figure 2G:
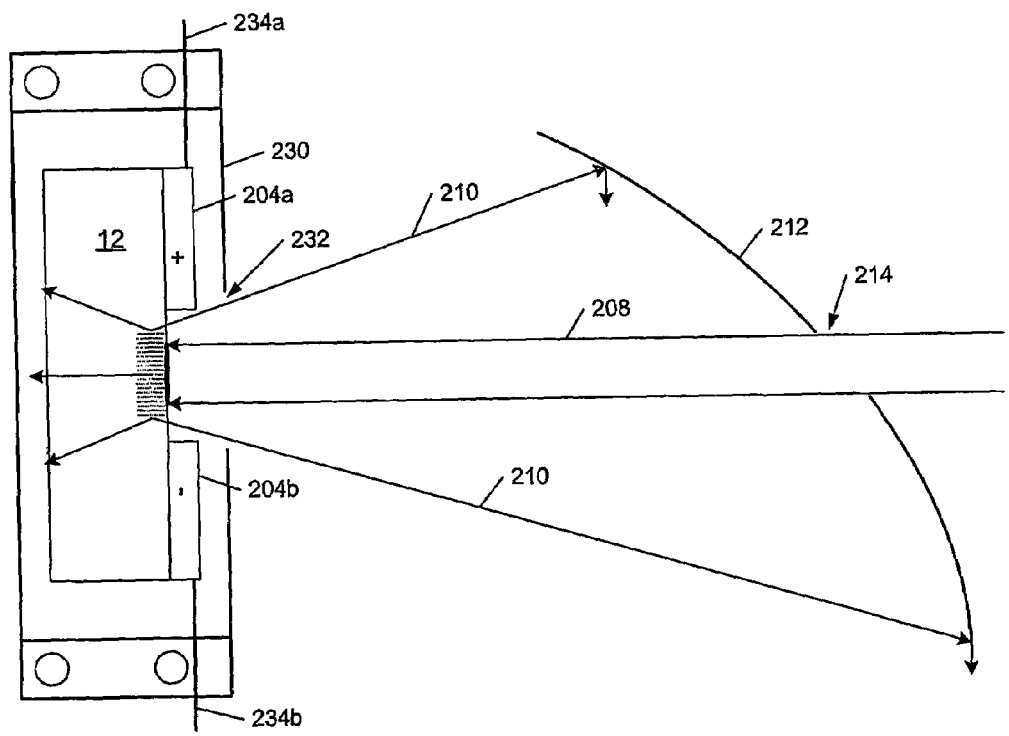

FIG. 2g illustrates an embodiment of a terahertz radiation source similar to that shown in FIG. 2a to 2c, but contained within a housing 230. An aperture 232 is provided in the housing to permit ingress of the pump laser beam 208 and egress of the terahertz radiation 210. Insulated connections 234a, b may be provided for electrodes 204a, b respectively. The housing 230 may be fabricated, for example, from metal, and optionally the housing may be extended to include the parabolic mirror 212 or, in other embodiments, a terahertz lens. A window may be provided for the pump laser beam and, optionally, a further window for the terahertz radiation (for example, using lens material), to allow the enclosure to be sealed.

Figure 3A:
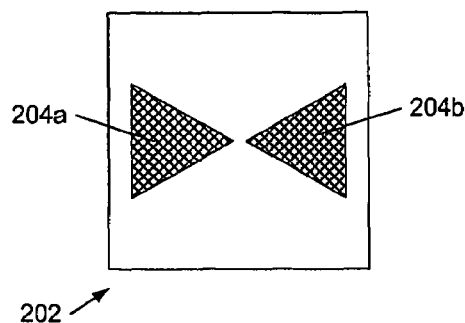
FIGS. 3a to 3c show, respectively, a first alternative electrode arrangement, a second alternative electrode arrangement, and an electrode drive voltage waveform.
Figure 3B:
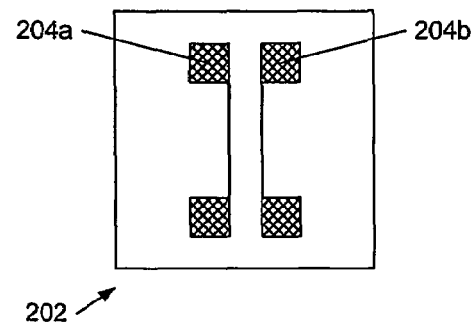
Figure 3C:
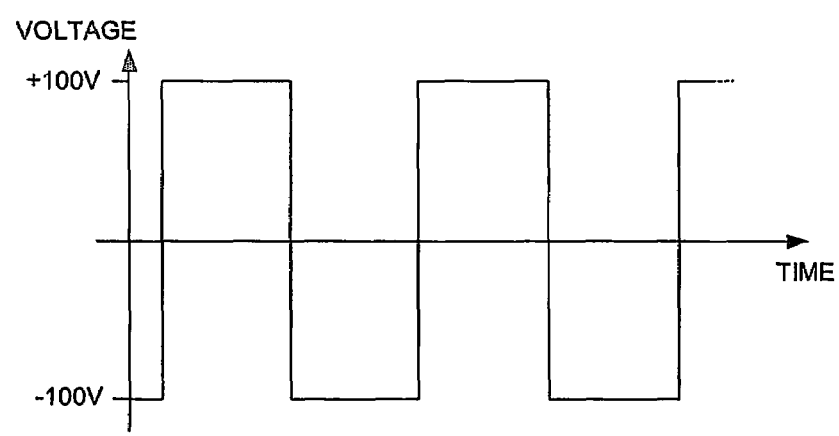

FIGS. 3a and 3b show some examples of alternative electrode configurations for the emitter 202; these may replace the configuration of FIG. 2b in the above described embodiments. FIG. 3c illustrates one example of a drive voltage which may be applied to the electrodes, in this example comprising a 100 KHz square wave symmetrical about 0 volts. The drive waveform is preferably symmetrical although asymmetric and dc voltages may also be employed.

As previously mentioned, in operation the terahertz source dissipates up to a few watts of electrical power. This can cause very large local increases in the temperature of semiconductor material 12, which can lower electron mobility. On a more practical level differential heating can bend the emitter and can damage the attachment of the electrodes 204 to the surface of the semiconductor. It is therefore preferable to cool the semiconductor, and FIGS. 4a and 4b illustrate some examples of cooling arrangements.

Figure 4A:
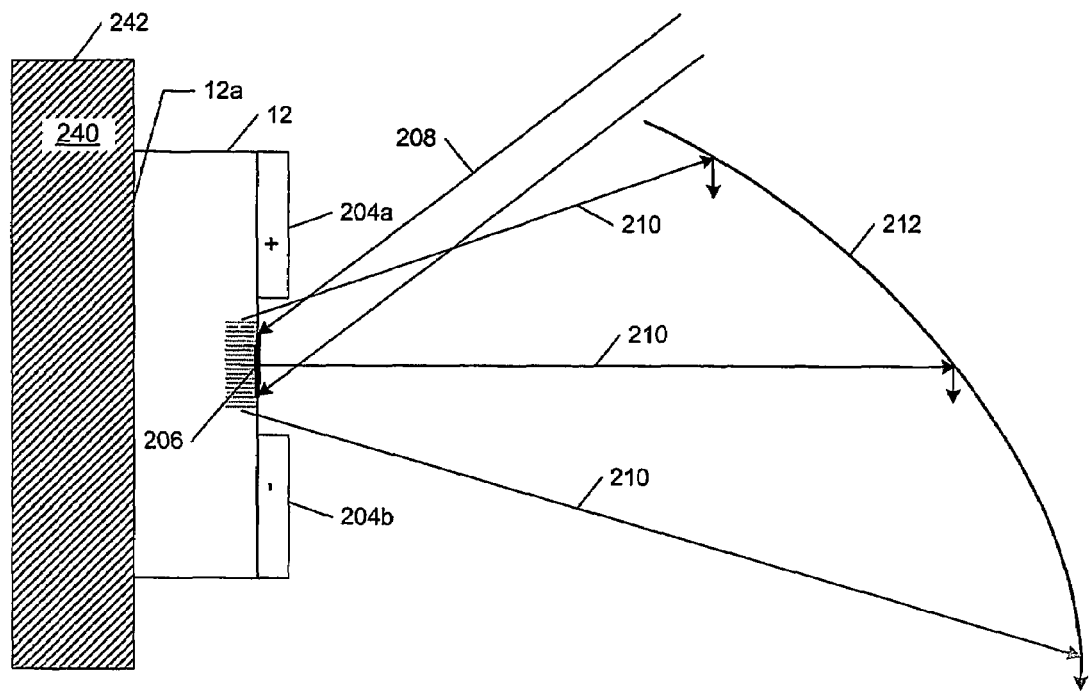
FIGS. 4a and 4b show, respectively, a first radiation source cooling arrangement, and a second radiation source cooling arrangement.

In FIG. 4a water 240 is pumped through ducting at 242 (shown schematically in FIG. 4a) in thermal contact with semiconductor 12. It is known to cool a terahertz radiation source to increase the available terahertz power (see G. Zhao, R. N. Schouten, N. van der Valk, W. Th. Wenckebach, and P. C. M. Planken, Rev. Sci. Instrum. 73, 1715, 2002; and Phys. Med. Biol. 47, 3699, 2002) but the effectiveness of such cooling has previously been limited by the need to make provision for the emission of terahertz radiation as shown in FIGS. 1a and 1b. Thus the effectiveness of the cooling has been limited. The skilled person will appreciate, however, that with the above described embodiments of the invention good thermal contact may be achieved between face 12a of the semiconductor and a heat sink or heat conductor such as ducting 242. More particularly the ducting 242 or other heat transfer arrangement may extend across face 12a of the emitter behind the gap between electrodes 204a, b.

Figure 4B:
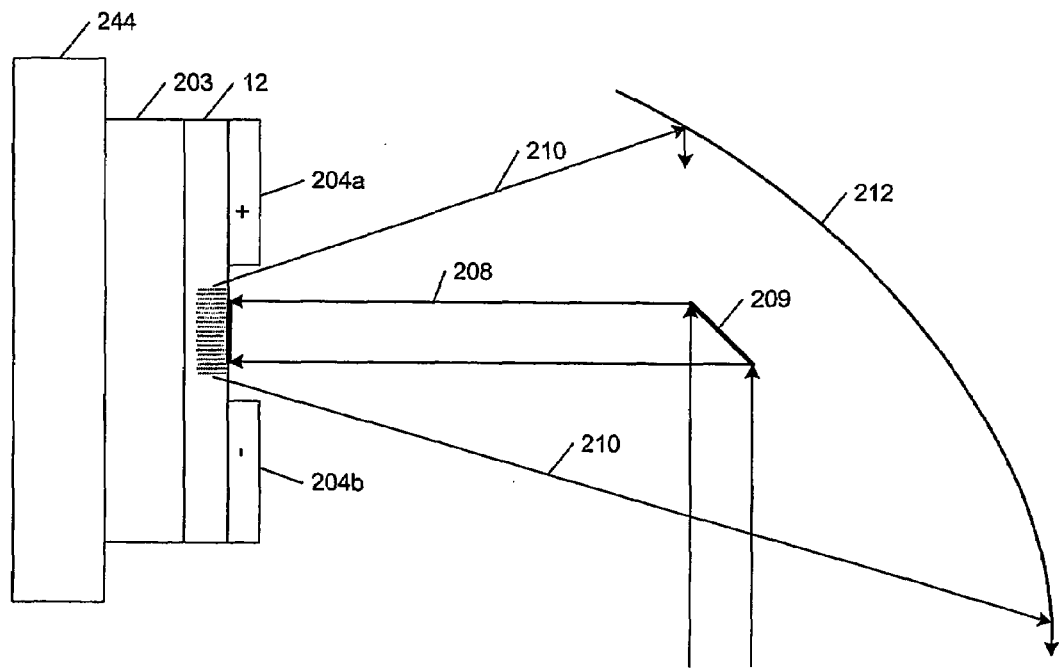

FIG. 4b shows a second example of a cooled terahertz radiation source in which semiconductor 12 is mounted on a substrate 203 which, in turn, is in thermal contact with a Peltier-effect cooling device 244 electrically driven to cool the terahertz emitter.

Again the Peltier-effect device may extend across the terahertz emitter, and in particular across the gap between the electrodes on the opposite side of the emitter to the electrodes. The skilled person will understand that many other types of similar cooling arrangement may be employed, including passive cooling such as fins or a heat sink, for example using housing 230 of FIG. 2g.

Some examples of experiments performed using arrangements similar to that shown in FIGS. 2a to 2c will now be described.

Referring again to FIG. 2a, in one experiment a bias voltage of 200 $V_{P-P}$, modulated at 31 KHz, was applied across the emitter 202. An average power of 250 mW from a Ti:Sapphire laser (14 fs duration, 800 nm center wavelength, and 76 MHz repetition rate) was focused onto the edge of one of the two NiCr/Au electrodes 204a,b of GaAs emitter 202. The spot size of the focused laser beam was 40 µm giving a maximum free carrier concentration of about $3 \times 10^{18}$ $cm^3$ (assuming 50% quantum efficiency and 1 µm average absorption depth). Increased power may be available from larger laser excitation spot sizes (see G. Zhao, R. N. Schouten, N. van der Valk, W. Th. Wenckebach, and P. C. M. Planken, Rev. Sci. Instrum. 73, 1715, 2002; and Phys. Med. Biol. 47, 3699, 2002).

The ultrafast acceleration and deceleration of the carriers in the electric field leads to the radiation of a THz electromagnetic signal into free space. The THz radiation was collected backwards (in the direction of the reflected pump laser beam) using off-axis parabolic mirror 212. The backwards collection scheme minimizes the absorption and dispersion of the THz pulse in the GaAs substrate.

After reflecting from four off-axis parabolic mirrors 212, 215, 217, 218, the THz pulse was finally focused onto 0.2-mm-thick GaP crystal 220 (from Photox Optical Systems of Oxford, UK) where it overlaps with a synchronized, time-delayed, horizontally polarized probe beam from the same laser source. The electric field of the THz transients induces birefringence in the GaP crystal, and changes the polarization of the probe beam. After the sensor, the probe beam then passes through quarter wave plate 222 and Wollaston prism 224. The Wollaston prism separates the two orthogonal polarization components of the probe beam, whose intensities are measured with a pair of balanced photodiodes 226a,b. The electro-optic signal ($\Delta I$) is normalized to the total photocurrent (I) from the two photodiodes, and the intensity difference $\Delta I/I$ is proportional to the THz electric field presented in the electro-optic crystal (see, for example, Q. Wu and X.-C. Zhang, Appl. Phys. Lett. 67, 3523, 1995).

In the arrangement of FIG. 2a the temporal (time-domain) information on the THz radiation may be obtained by varying the time difference between excitation of the carriers and probing of the field, for example by means of a variable optical delay stage (not shown), in one experiment with an accuracy of 0.1 µm. The apparatus of FIG. 2a is preferably enclosed in a vacuum-tight box, which is purged with dry nitrogen gas to reduce the effects of water vapor absorption. The described experiments were performed at room temperature.

FIG. 5a shows THz radiation collected backwards from an LT-GaAs emitter and measured with a 0.2-mm-thick GaP crystal as a function of delay time. A signal-to-noise ratio of over 1000 was easily obtained using a lock-in amplifier with a time constant of 20 ms. The skilled person will appreciate the narrowness of the terahertz pulses (140 fs and 105 fs) in FIG. 5a.

FIG. 5b shows a THz signal from the same emitter under similar conditions, but measured using a conventional, forwards collection scheme. As shown in FIG. 5b the shape of the THz transient is distorted owing to dispersion and absorption in the GaAs substrate. Ringing can also be seen, due to dispersion and absorption of the terahertz radiation within the GaAs substrate. In addition, about 10 picoseconds after the main terahertz peak, a second terahertz peak is observed, due to multiple reflections of the terahertz radiation at the air/GaAs interfaces. For a slab of thickness d, the interval between pulses is approximately 2d/c where c is the speed of radiation in the substrate. The embodiments of FIG. 2 allow a relatively thick substrate to be employed, thus reducing this ringing without also increasing the attenuation and distortion, which would otherwise be seen in a conventional, forwards-collection configuration.

FIG. 5c shows, on a logarithmic scale, the amplitude spectra of the transients of FIGS. 2a and 2b, curve 500 corresponding to FIG. 5a and curve 502 to FIG. 5b. As can be seen, curve 502 is effectively in the noise above around 6 THz whilst curve 500 shows that with embodiments of the invention terahertz radiation may be provided up to at least 10 THz (the dip at approximately 8 THz is caused by a phonon absorption in the GaAs).

Still referring to FIG. 5c, the spectrum 500 peaks at about 2 THz and spreads continuously up to 8 THz. Some amplitude is then regained for frequencies around 9 THz, particularly a distinct peak at 8.7 THz, despite the low sensitivity of the GaP detector in this frequency range. By contrast the high frequency components are attenuated in the GaAs substrate in spectrum 502. It can therefore be appreciated that the "backwards" collection scheme reduces the effects of THz dispersion and absorption in the GaAs substrate.

The spectral dip at the TO (Transverse Optical) phonon of GaAs (8 THz) and the enhanced radiation at the LO (Longitudinal Optical) phonon of GaAs (8.7 THz) can be explained by the respective increase and reduction of the coupling efficiency of the radiation to the air due to the small and large absolute values of the complex dielectric constant near TO and LO phonon frequencies, respectively (see M. Tani, R. Fukasawa, H. Abe, K. Sakai and S. Nakashima, J. Appl. Phys. 83, 2473, 1998). In addition, although the first TO phonon of GaP crystal does not appear until 11 THz the frequency response of the GaP detector has a minimum around 8 THz owing to strong dispersion of the electro-optic coefficient $\gamma_{41}$ of the GaP crystal, due to lattice resonance. This may also contribute to the spectral dip at 8 THz observed in terahertz spectrum 500.

The amplitude and the phase response of a 0.2-mm-thick GaP sensor may be calculated taking into account reflection and absorption losses, the velocity mismatch between the optical gating pulse and the THz phase, and the dispersion of the electro-optic coefficient (see, for example, A. Leitenstorfer, S. Hunsche, J. Shah, M. C. Nuss, and W. H. Knox, Appl. Phys. Lett. 74, 1516, 1999). Such calculations show that the GaP detector employed here has limited sensitivity at frequencies above 8 THz. Therefore in order to explore the higher frequency characteristics of the GaAs emitter a different detector was employed. This comprised a 20-µm-thick (110) ZnTe crystal glued onto a (100) ZnTe crystal. FIGS. 6a and 6b show data collected using such a detector.

FIG. 6a shows THz radiation, measured with a 20-µm-thick ZnTe detector, as a function of time, and FIG. 6b shows, on a logarithmic scale, corresponding terahertz radiation spectra. Curves 600 and 602 of FIG. 6b were captured using a ZnTe detector and a GaP detector respectively.

The first main positive and negative peaks of the THz transient of FIG. 6a have pulse widths of 76 fs and 44 fs, respectively, which, to the best of the Applicant's knowledge, represents the shortest THz pulse yet reported for a GaAs photoconductive emitter. The THz spectra of FIG. 6b show a number of distinct dips and peaks. By comparing these with the spectrum of FIG. 5c it can be seen that the dip in curve 600 at around 5.2 THz is caused by the ZnTe detector (TO phonon at 5.3 THz) whilst the dip at 8.0 THz is due to the GaAs emitter (TO phonon at 8.0 THz). The two peaks at 6.1 and 8.7 THz correspond to the LO phonon of ZnTe (6.2 THz) and GaAs (8.7 THz), respectively. FIG. 6b shows that frequency components of up to 18 THz can be generated using a LT-GaAs-based emitter which, to the best of the Applicant's knowledge, is the highest frequency component from a biased photoconductive emitter yet reported.

FIG. 7a shows a time-domain terahertz signal obtained using the above-described apparatus, and FIGS. 7b and 7c show corresponding frequency spectra, FIG. 7b having a linear amplitude scale, and FIG. 7c a logarithmic scale. More particularly FIGS. 7a to 7c show the absorption of terahertz radiation by different semiconductor materials, as determined using the above apparatus with the semiconductor in the sample position. FIGS. 7b and 7c relate to terahertz radiation transmitted through a HR (high resistivity) silicon wafer whilst curve 702 relates to transmission through a SI (semi-insulating) GaAs wafer, both from an LT (low-temperature-grown) GaAs photoconductive emitter. It can be seen that these curves have been determined for frequencies extending out beyond 30 THz, albeit with reduced signal-to-noise ratio at higher frequencies. This is useful for many applications including, for example, detecting (and studying) intra-molecular vibrations.

Figure 8A:
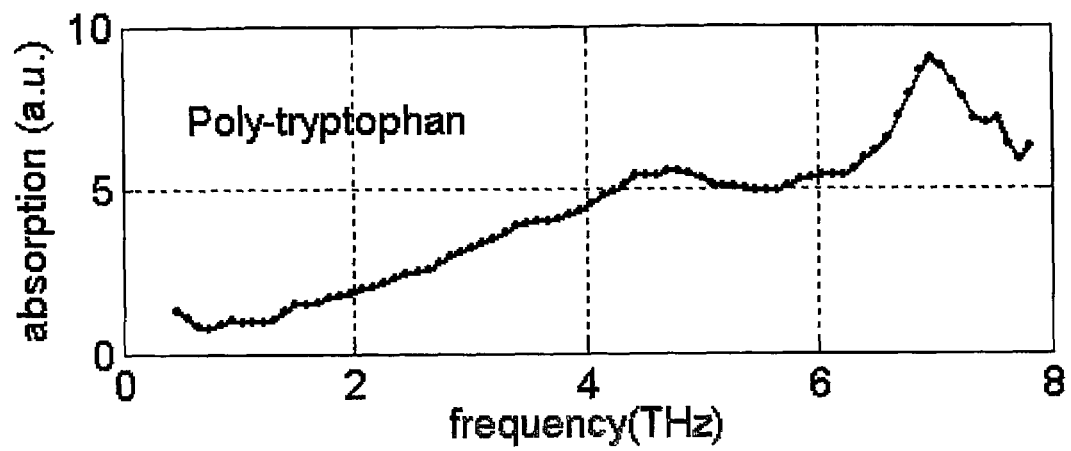
FIGS. 8a and 8b show, respectively, a example of a terahertz absorption spectrum of an amino acid, and a terahertz absorption spectrum of PTFE.
Figure 8B:
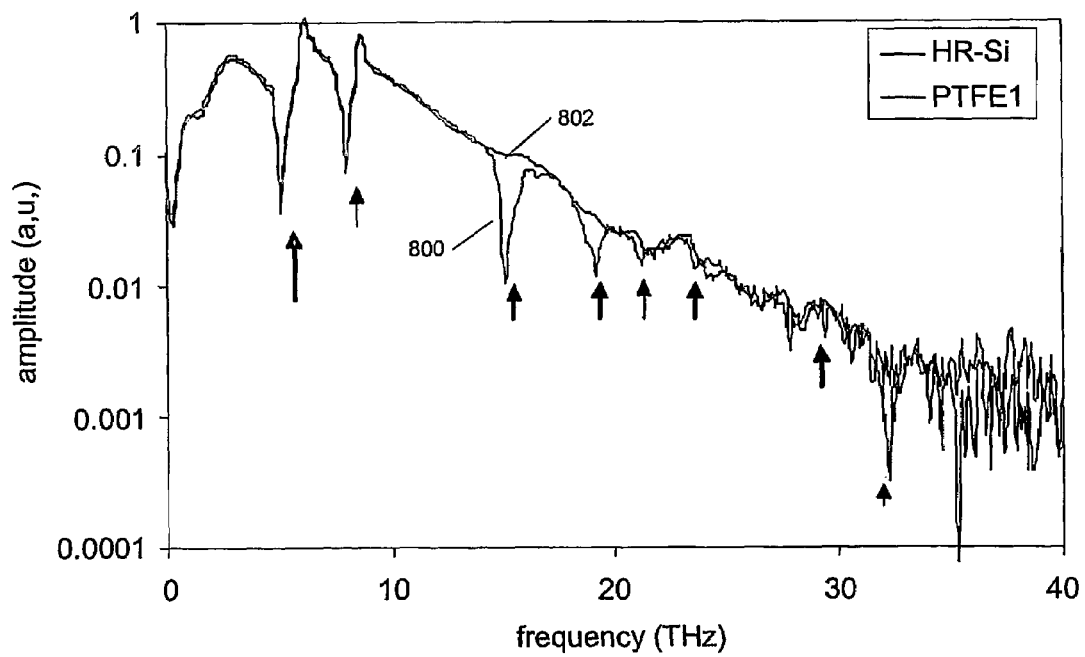

FIGS. 8a and 8b show some examples of applications of the above described terahertz radiation sources. FIG. 8a shows a THz spectrum of poly-L-Tryptophan (an important amino acid homo-polymer) measured in the frequency range 0.2-7.8 THz using a terahertz radiation source as described above. The broad peak around 5 THz and the relatively narrower peak at around 7 THz are in good agreement with observations made using inelastic neutron scattering techniques. FIG. 8b shows an absorption spectrum 800 of PTFE (polytetrafluoroethylene) alongside the source spectrum 802 (of HR-Si), showing vibrational absorption bands. Again this is in good agreement with known absorption bands, at 15.1, 19.2, 21.2 23.7, 29.4 and 32.3 THz (see Vibrational Spectroscopy 26(2001)215-25), marked by arrows. The extended frequency range provided by embodiments of the invention has many applications including in both time- and frequency-domain spectroscopy where it can provide an overlap with Fourier transform, Raman and inelastic neutron scattering spectroscopy thus assisting an understanding of intra- and inter-molecular interactions.

No doubt many other effective alternatives to the described embodiments will occur to the skilled person. It will therefore be understood that the invention is not limited to the described embodiments but encompasses modifications apparent to those skilled in the art lying within the spirit and scope of the claims appended hereto.

The invention claimed is:

1. A terahertz radiation source comprising:
an emitter comprising a semiconductor material having two sides;
a pair of electrodes on one side of said semiconductor;
a pulsed light source input for illuminating said semiconductor to excite photocarriers in said semiconductor to generate terahertz radiation; and
a radiation collector to collect said terahertz radiation; and
wherein said radiation collector is disposed on the same side of said semiconductor as said electrodes and said light pulsed source impinges on the same side of said semiconductor as said electrodes.

2. A terahertz radiation source comprising:
a semiconductor having opposed first and second faces;
a pair of electrodes adjacent one of said faces of said semiconductor;
a pulsed light source input for illuminating said one of said faces of said semiconductor to excite photo-carriers in said semiconductor to generate terahertz radiation; and
a radiation collector to collect said terahertz radiation; and
wherein said radiation collector is configured to collect said terahertz radiation from said one of said faces of said semiconductor without said collected radiation having passed through the other of said faces.

3. A terahertz radiation source as claimed in claim 1 wherein said radiation collector comprises a mirror.

4. A terahertz radiation source as claimed in claim 1 wherein said radiation collector comprises a lens.

5. A terahertz radiation source as claimed in claim 1 wherein said radiation collector has an aperture for illuminating said semiconductor through said radiation collector.

6. A terahertz radiation source as claimed in claim 1 further comprising a diagonal mirror disposed between said semiconductor and said radiation collector for illuminating said semiconductor.

7. A terahertz radiation source as claimed in claim 1 further comprising a cooling device in thermal contact with said emitter and disposed on an opposite side of said semiconductor material to said electrodes.

8. A terahertz radiation source as claimed in claim 7 wherein said pair of electrodes defines a gap between said electrodes, and wherein said cooling device is disposed opposite said gap.

9. A terahertz radiation source as claimed in claim 1 further comprising a pulsed laser to provide light to said pulsed light source input.

10. A source of terahertz radiation comprising:
a housing, said housing holding a semiconductor, said semiconductor bearing a pair of electrodes adjacent one surface of said semiconductor;
means for directing a pulsed laser onto said electrode-bearing semiconductor to generate terahertz radiation; and
means for providing said terahertz radiation from said source; and
characterised in that said providing means is disposed to face said electrode-bearing semiconductor surface.

11. A source of terahertz radiation as claimed in claim 10 wherein said means for providing terahertz radiation comprises an aperture in said housing.

12. A source of terahertz radiation as claimed in claim 10 wherein said means for providing terahertz radiation includes a terahertz radiation focusing device.

13. A source of terahertz radiation as claimed in claim 12 wherein said means for directing said pulsed laser onto said semiconductor includes an aperture in said focusing device.

14. A source of terahertz radiation as claimed in claim 10 wherein said means for directing said pulsed laser onto said semiconductor comprises an aperture in said housing.

15. A source of terahertz radiation as claimed in claim 10 further comprising a heat transfer device for cooling said semiconductor, said heat transfer device being disposed opposite said electrode-bearing semiconductor surface.

16. A source of terahertz radiation as claimed in claim 10 for providing terahertz radiation within a portion of a frequency range of from 0.1 THz to 100 THz, more particularly within a portion of a frequency range of from 0.1 THz to 30 THz.

17. A terahertz emitter comprising:
a semiconductor having first and second electrodes adjacent a first face of said semiconductor for applying an electric field to the semiconductor, said first and second electrodes defining a gap therebetween; and
a heat transfer device mounted adjacent a second face of said semiconductor substantially opposite said first face; and
wherein at least a portion of said heat transfer device is disposed substantially opposite said gap.

18. A terahertz emitter as claimed in claim 17 wherein said heat transfer device comprises an active cooling device.

19. A terahertz emitter as claimed in claim 18 wherein said heat transfer device comprising a Peltier effect cooling device.

20. A terahertz radiation source or emitter as claimed in claim 1 wherein said semiconductor comprises a compound semiconductor.

21. A terahertz radiation source or emitter as claimed in claim 20, wherein said semiconductor comprises gallium arsenide.

22. A method of providing terahertz radiation from a photoconductive terahertz radiation source, the source comprising a semiconductor with electrodes adjacent an excitation surface of the said semiconductor, the method comprising:
applying an electric field to said electrodes;
directing a pulsed laser beam towards said excitation surface; and
using terahertz radiation emitted out of said excitation surface for providing said terahertz radiation.

23. A method of providing terahertz radiation from a photoconductive terahertz radiation source, the source comprising a semiconductor with electrodes adjacent a surface of the said semiconductor, the method comprising:
applying an electric field to said electrodes; and
directing a pulsed laser beam towards said semiconductor surface,
wherein a normal to said semiconductor surface with a component in a direction of propagation of said laser beam defines a forward direction; and wherein the method further comprises:
collecting said terahertz radiation in a reverse direction, substantially opposite to said forwards directions.

* * * * *